(12) United States Patent
Ye et al.

(10) Patent No.: US 10,890,640 B2
(45) Date of Patent: Jan. 12, 2021

(54) SYSTEMS AND METHODS FOR SIGNAL REPRESENTATION DETERMINATION IN MAGNETIC RESONANCE IMAGING

(71) Applicant: UIH AMERICA, INC., Houston, TX (US)

(72) Inventors: Yongquan Ye, Houston, TX (US); Jingyuan Lyu, Houston, TX (US)

(73) Assignee: UIH AMERICA, INC., Houston, TX (US)

( * ) Notice: Subject to any disclaimer, the term of this patent is extended or adjusted under 35 U.S.C. 154(b) by 0 days.

(21) Appl. No.: 16/357,313

(22) Filed: Mar. 18, 2019

(65) Prior Publication Data
US 2020/0300951 A1 Sep. 24, 2020

(51) Int. Cl.
*G01R 33/50* (2006.01)
*G01R 33/561* (2006.01)
*G01R 33/56* (2006.01)
*A61B 5/055* (2006.01)

(52) U.S. Cl.
CPC .............. *G01R 33/50* (2013.01); *A61B 5/055* (2013.01); *G01R 33/561* (2013.01); *G01R 33/5608* (2013.01)

(58) Field of Classification Search
CPC .. G01R 33/50; G01R 33/5608; G01R 33/561; A61B 5/055
See application file for complete search history.

(56) References Cited

U.S. PATENT DOCUMENTS

| 6,388,441 B1 | 5/2002 | Chen | |
|---|---|---|---|
| 2010/0086184 A1* | 4/2010 | Kruger | G01R 33/54 382/128 |
| 2011/0105884 A1* | 5/2011 | Beck | G01R 33/561 600/410 |
| 2018/0017652 A1 | 1/2018 | Ye | |
| 2018/0081004 A1 | 3/2018 | Yang | |

(Continued)

FOREIGN PATENT DOCUMENTS

CN 108294753 A 7/2018

OTHER PUBLICATIONS

Bidhult, S et al., Validation of a new T2* algorithm and its uncertainty value for cardiac and liver iron load determination from MRI magnitude images. Magnetic Resonance in Madicine, 75: 1717-1729(2016).

(Continued)

*Primary Examiner* — Susan S Lee
(74) *Attorney, Agent, or Firm* — Metis IP LLC

(57) ABSTRACT

A method for determining a signal representation of a subject in MRI is provided. The method may include acquiring a plurality of signals of the subject. The plurality of signals may be generated using an MRI device, and each of the plurality of signals may correspond to a set of values in a plurality of signal dimensions of signal acquisition using the MRI device. The method may include determining, among the plurality of signal dimensions, a primary signal dimension and at least one secondary signal dimension, the primary signal dimension being associated with the signal representation. The method may also include determining the signal representation of the subject based on the primary signal dimension, the at least one secondary signal dimension, and the plurality of signals.

20 Claims, 9 Drawing Sheets

(56) References Cited

U.S. PATENT DOCUMENTS

| | | | |
|---|---|---|---|
| 2018/0143272 A1* | 5/2018 | Liu | G01R 33/36 |
| 2018/0231631 A1 | 8/2018 | Ye et al. | |
| 2018/0275235 A1 | 9/2018 | Reeder et al. | |
| 2018/0338701 A1* | 11/2018 | Amemiya | A61B 5/02007 |
| 2019/0318511 A1 | 10/2019 | Ye | |
| 2020/0090382 A1* | 3/2020 | Huang | G06T 11/006 |
| 2020/0126231 A1 | 4/2020 | Hu et al. | |

OTHER PUBLICATIONS

Hesper, T et al., T2* mapping for articular cartilage assessment: principles, current applications, and future prospects. Skeletal Radiol, 43: 1429-1445(2014).

Wu, Bing et al., Fast and tissue-optimized mapping of magnetic susceptibility and T2* with multi-echo and multi-shot spirals. Neuroimage, Author manuscript, available in PMC Jan. 2, 2013 59(1): 21(2012).

Ajay Kumar Boyat et al., A Review Paper: Noise Models in Digital Image Processing, Signal & Image Processing: An International Journal, 6(2): 63-75, 2015.

Xiang Qing-San, Two-Point Water-Fat Imaging With Partially-Opposed-Phase (POP) Acquisition: An Asymmetric Dixon Method, Magnetic Resonance in Medicine, 56: 572-584, 2006.

Scott B. Reeder et al., Homodyne Reconstruction and IDEAL Water-Fat Decomposition, Magnetic Resonance in Medicine, 54: 586-593, 2005.

Gary H. Glover, Multipoint Dixon Technique for Water and Fat Proton and Susceptibility Imaging, Journal of Magnetic Resonance Imaging, 1(5): 521-530, 1991.

J.B.M. Warntjes et al., Rapid Magnetic Resonance Quantification on the Brain: Optimization for Clinical Usage, Magnetic Resonance in Medicine, 60: 320-329, 2008.

J.B.M. Warntjes et al., Novel Method for Rapid, Simultaneous T1, T2*, and Proton Density Quantification, Magnetic Resonance in Medicine, 57: 528-537, 2007.

Wang Yu et al., STrategically Acquired Gradient Echo (STAGE) Imaging, part II: Correcting for RF Inhomogeneities in Estimating T1 and Proton Density, Magnetic Resonance Imaging, 46: 140-150, 2018.

Chen Yongsheng et al., Strategically Acquired Gradient Echo (STAGE) imaging, part I: Creating Enhanced T1 Contrast and Standardized Susceptibility Weighted Imaging and Quantitative Susceptibility Mapping, Magnetic Resonance Imaging, 46: 130-139, 2018.

Ma Dan et al., Magnetic Resonance Fingerprinting, Nature, 495: 187-192, 2013.

Vasily L. Yarnykh, Actual Flip-angle Imaging in the Pulsed Steady State: A Method for Rapid Three-dimensional Mapping of the Transmitted Radiofrequency Field, Magnetic Resonance in Medicine, 57: 192-200, 2007.

Kay Nehrke, On the Steady-state Properties of Actual Flip Angle Imaging (AFI), Magnetic Resonance in Medicine, 61: 84-92, 2009.

Sean C.L. Deoni, High-Resolution T1 Mapping of the Brain at 3T with Driven Equilibrium Single Pulse Observation of T1 with High-Speed Incorporation of RF Field Inhomogeneities (DESPOT1-HIFI), Journal of Magnetic Resonance Imaging, 26: 1106-1111, 2007.

Tokunori Kimura et al., Hybrid of Opposite-contrast MR Angiography (HOP-MRA) Combining Time-of-flight and Flow-Sensitive Black-Blood Contrasts, Magnetic Resonance in Medicine, 62: 450-458, 2009.

Ye Yongquan et al., Noncontrast-Enhanced Magnetic Resonance Angiography and Venography Imaging With Enhanced Angiography, Journal of Magnetic Resonance Imaging, 38: 1539-1548, 2013.

* cited by examiner

600

┌─────────────────────────────────────────────────────────┐
│ Acquiring a plurality of signals of the subject, the plurality │
│ of signals being generated using an MRI device, each of │ ~602
│ the plurality of signals corresponding to a set of values in a │
│ plurality of signal dimensions of signal acquisition using the │
│ MRI device │
└─────────────────────────────────────────────────────────┘
                              ↓
┌─────────────────────────────────────────────────────────┐
│ Determining, among the plurality of signal dimensions, a │
│ primary signal dimension and at least one secondary │ ~604
│ signal dimension, the primary signal dimension being │
│ associated with the signal representation │
└─────────────────────────────────────────────────────────┘
                              ↓
┌─────────────────────────────────────────────────────────┐
│ Determining, based on the plurality of signals, the primary │ 606
│ signal dimension, and the at least one secondary signal │
│ dimension, the signal representation of the subject │
└─────────────────────────────────────────────────────────┘
                              ↓
┌ ─ ─ ─ ─ ─ ─ ─ ─ ─ ─ ─ ─ ─ ─ ─ ─ ─ ─ ─ ─ ─ ─ ─ ─ ─ ─ ─ ┐
│ Determining, based on the signal representation of the │ 608
│ subject, a value of the quantitative parameter of the subject │
└ ─ ─ ─ ─ ─ ─ ─ ─ ─ ─ ─ ─ ─ ─ ─ ─ ─ ─ ─ ─ ─ ─ ─ ─ ─ ─ ─ ┘

For at least one value in the at least one secondary signal dimension, determining, based on a portion of the plurality of signals that correspond to the at least one value of the at least one secondary signal dimension, at least one preliminary signal representation of the subject associated with the primary signal dimension —702

Determining, based on at least a portion of the at least one preliminary signal representation of the subject, the signal representation of the subject —704

Obtaining an optimization function of the signal representation of the subject, the optimization function incorporating the primary signal dimension and the at least one secondary signal dimension —706

Determining the signal representation of the subject by inputting the plurality of signals into the optimization function —708

SYSTEMS AND METHODS FOR SIGNAL REPRESENTATION DETERMINATION IN MAGNETIC RESONANCE IMAGING

TECHNICAL FIELD

The present disclosure generally relates to magnetic resonance imaging (MRI), and more particularly, methods and systems for determining a signal representation and/or a quantitative parameter of a subject in MRI.

BACKGROUND

MRI systems are widely used in medical diagnosis and/or treatment by exploiting a powerful magnetic field and radio frequency (RF) techniques. In an MR scan of a subject, a plurality of coil units of an MRI device may detect a plurality of echo signals representing a plurality of echoes after an MR pulse sequence is applied on the subject. In some occasions, one or more parameters, such as a longitudinal relaxation time (T1), a transverse relaxation time (T2), and a transverse relaxation decay (T2*) of the subject may be determined based on the echo signals. The quantitative parameter(s) may reflect physiological characteristics of the subject and be used in disease diagnosis. Conventionally, a series of images may be reconstructed for each coil unit based on the corresponding echo signals. The images of different coil units corresponding to the same echo may be combined into an echo image, for example, using a sum of square (SOS) algorithm or an adaptive coil combination (ACC) algorithm. The quantitative parameter(s) may then be determined based on the echo images corresponding to different echoes using a data fitting algorithm. However, this is an inefficient way for quantitative parameter determination and the determination result is sometimes inaccurate.

Normally, a quantitative parameter of a subject may be associated with a signal representation of the subject acquired or determined in an examination or imaging of the subject. Such a signal representation of the subject may also reflect one or more physiological characteristics of the subject, which can be used in diseases diagnosis directly and/or in the determination of the quantitative parameter. Therefore, it is desirable to develop effective systems and methods to determine a signal representation and/or a quantitative parameter of the subject based on an examination or imaging technology.

SUMMARY

In one aspect of the present disclosure, a system is provided. The system may include at least one storage medium including a set of instructions for determining a signal representation of a subject in MRI. The system may further include at least one processor configured to communicate with the at least one storage medium. When executing the set of instructions, the at least one processor may be configured to direct the system to acquire a plurality of signals of the subject. The plurality of signals may be generated using an MRI device, and each of the plurality of signals may correspond to a set of values in a plurality of signal dimensions of signal acquisition using the MRI device. The at least one processor may be also configured to direct the system to determine, among the plurality of signal dimensions, a primary signal dimension and at least one secondary signal dimension, the primary signal dimension being associated with the signal representation. The at least one processor may be further configured to direct the system to determine the signal representation of the subject based on the plurality of signals, the primary signal dimension, and the at least one secondary signal dimension.

In some embodiments, to determine the signal representation of the subject, the at least one processor may be further configured to direct the system to, for at least one value in the at least one secondary signal dimension, determine at least one preliminary signal representation of the subject associated with the primary signal dimension based on a portion of the plurality of signals that correspond to the value of the at least one secondary signal dimension. The at least one processor may be further configured to direct the system to determine the signal representation of the subject based on at least a portion of the at least one preliminary signal representation of the subject.

In some embodiments, to determine the signal representation of the subject, the at least one processor may be further configured to direct the system to obtain an optimization function of the signal representation of the subject, the optimization function incorporating the primary signal dimension and the at least one secondary signal dimension. The at least one processor may be further configured to direct the system to determine the signal representation of the subject by inputting the plurality of signals into the optimization function.

In some embodiments, to determine the signal representation of the subject by inputting the plurality of signals into the optimization function, the at least one processor may be further configured to direct the system to, for at least one value in the at least one secondary signal dimension, determine, among the plurality of signals, at least one pair of signals corresponding to the value in the at least one secondary signal dimension, wherein each pair of the at least one pair of signals corresponds to different values in the primary signal dimension. The at least one processor may be further configured to direct the system to determine the signal representation of the subject by inputting the at least one pair of signals into the optimization function.

In some embodiments, to determine the signal representation of the subject by inputting the plurality of signals into the optimization function, the at least one processor may be further configured to direct the system to cause the MRI device to apply an MR pulse sequence on the subject. The at least one processor may be further configured to direct the system to detect a plurality of echo signals by at least one coil units of the MRI device. The at least one processor may be further configured to direct the system to determine the plurality of signals of the subject based on the plurality of echo signals.

In some embodiments, the subject may be a physical point of an object, and to determine the plurality of signals of the subject based on the plurality of echo signals, the at least one processor may be further configured to direct the system to reconstruct a plurality of images including image data of the physical point based on the plurality of echo signals. The at least one processor may be further configured to direct the system to designate the image data corresponding to the physical point in the plurality of images as the plurality of signals of the physical point.

In some embodiments, the signal representation of the subject may be associated with a quantitative parameter of interest. The primary signal dimension may be associated with the quantitative parameter of interest. The at least one secondary signal dimension may be not associated with the quantitative parameter of interest. The at least one processor may be further configured to direct the system to determine a value of the quantitative parameter of interest of the subject based on the signal representation of the subject.

In some embodiments, to determine a value of the quantitative parameter of interest of the subject, the at least one processor may be further configured to direct the system to obtain a relationship relating to signal representations of the subject and values of the quantitative parameter of interest. The at least one processor may be further configured to direct the system to determine the value of the quantitative parameter of interest of the subject based on the signal representation of the subject and the relationship.

In some embodiments, the subject may be a physical point of an object. The signal representation may be a change of signal intensity at the physical point with an echo time. The quantitative parameter of interest of the physical point may include at least one of a longitudinal relaxation time, a transverse relaxation time, an apparent diffusion coefficient (ADC), a transverse relaxation decay, a field distribution, or a longitudinal relaxation time in a rotating frame.

In some embodiments, the primary signal dimension may be an echo time, and the quantitative parameter of interest may be at least one of the transverse relaxation time, the transverse relaxation decay, or the field distribution. Alternatively, the primary signal dimension may be a T2-preparation duration, and the quantitative parameter of interest may be the transverse relaxation time. Alternatively, the primary signal dimension may be a T1ρ-preparation duration, and the quantitative parameter of interest may be the longitudinal relaxation time in a rotating frame. Alternatively, the primary signal dimension may be an inversion time, and the quantitative parameter of interest may be the longitudinal relaxation time. Alternatively, the primary signal dimension may be a b-value, and the quantitative parameter of interest may be the ADC.

In some embodiments, the signal representation may be represented by a complex number including a phase component and an amplitude component, and the value of the quantitative parameter of interest may be determined based on at least one of the phase component or the amplitude component of the complex number. Alternatively, the signal representation may be represented by a real number, and the value of the quantitative parameter of interest may be determined based on the real number.

In some embodiments, the plurality of signal dimensions may include at least two of an echo time (TE), an unit repetition time (TR), an inversion recovery time (TI), a b-value, a T1ρ-preparation duration, a T2-preparation duration, a repetition, a velocity encoding value, a count of radio frequency (RF) channels, a flip angle, an RF center frequency, or a RF receiving coil unit.

In another aspect of the present disclosure, a method is provided. The method may be implemented on a computing device having at least one processor and at least one computer-readable storage medium including a set of instructions for determining a signal representation of a subject in MRI. The method may include acquiring a plurality of signals of the subject. The plurality of signals may be generated using an MRI device, and each of the plurality of signals may correspond to a set of values in a plurality of signal dimensions of signal acquisition using the MRI device. The method may include determining, among the plurality of signal dimensions, a primary signal dimension and at least one secondary signal dimension, the primary signal dimension being associated with the signal representation. The method may also include determining the signal representation of the subject based on the primary signal dimension, the at least one secondary signal dimension, and the plurality of signals.

In yet another aspect of the present disclosure, a non-transitory computer-readable storage medium may include at least one set of instructions for determining a signal representation of a subject in MRI. When executed by at least one processor of an electrical device, the at least one set of instructions may direct the at least one processor to perform a method. The method may include acquiring a plurality of signals of the subject. The plurality of signals may be generated using an MRI device, and each of the plurality of signals may correspond to a set of values in a plurality of signal dimensions of signal acquisition using the MRI device. The method may also include determining, among the plurality of signal dimensions, a primary signal dimension and at least one secondary signal dimension, the primary signal dimension being associated with the signal representation. The method may also include determining the signal representation of the subject based on the plurality of signals, the primary signal dimension, and the at least one secondary signal dimension.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 6 is a flowchart illustrating an exemplary process for determining a signal representation of a subject according to some embodiments of the present disclosure;

FIGS. 7A and 7B are flowcharts illustrating exemplary processes for determining a signal representation of a subject according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "device," "unit," "module," and/or "block" used herein are one method to distinguish different components, elements, parts, section or assembly of different level in ascending order. However, the terms may be displaced by another expression if they achieve the same purpose.

Figure 3:
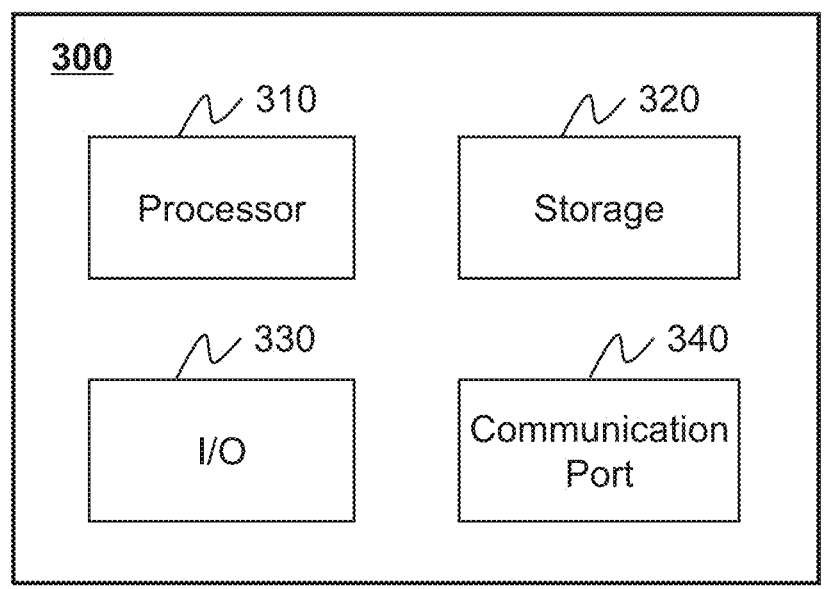
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, a device, or a portion thereof.

It will be understood that when a unit, device, module or block is referred to as being "on," "connected to," or "coupled to," another unit, device, module, or block, it may be directly on, connected or coupled to, or communicate with the other unit, device, module, or block, or an intervening unit, device, module, or block may be present, unless the context clearly indicates otherwise. As used herein, the term "and/or" includes any and all combinations of one or more of the associated listed items. The term "pixel" and "voxel" in the present disclosure are used interchangeably to refer to an element in an image. The term "image" in the present disclosure is used to refer to images of various forms, including a 2-dimensional image, a 3-dimensional image, a 4-dimensional image, etc.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in inverted order, or simultaneously. Moreover, one or more other operations may be added to the flowcharts. One or more operations may be removed from the flowcharts.

Moreover, while the systems and methods disclosed in the present disclosure are described primarily regarding determining a signal representation and/or a value of a quantitative parameter of a subject (e.g., a patient, a physical point of the patient) in an MRI system. It should be understood that this is only for illustration purposes. The systems and methods of the present disclosure may be applied to any other kind of medical imaging system. In some embodiments, the imaging system may include a single modality imaging system and/or a multi-modality imaging system. The single modality imaging system may include, for example, the MRI system. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc.

An aspect of the present disclosure relates to systems and methods for determining a signal representation of a subject. The signal representation may refer to a representative value or an attribute value of one or more echo signals of the subject detected in an MR scan of the subject. The signal representation may reflect one or more physiological characteristics or physical characteristics of the subject, which may provide a basis for medical diagnosis and/or treatment. The systems and methods may acquire a plurality of signals (e.g., K-space data or image data) of the subject. The signals may be generated using an MRI device and each signal may correspond to a set of values in a plurality of signal dimensions of signal acquisition using the MRI device. The systems and methods may also determine, among the plurality of signal dimensions, a primary signal dimension and at least one secondary signal dimension. The primary signal dimension may be associated (or correlate) with the signal representation. The systems and methods may further determine the signal representation of the subject based on the plurality of signals, the primary signal dimension, and the at least one secondary signal dimension. Moreover, in some embodiments, the systems and methods may further determine a value of a quantitative parameter (e.g., T2*, T2, and/or T1) of the subject, which may be used in, e.g., diagnosis.

According to some embodiments of the present disclosure, the signal representation of the subject is determined by jointly processing signals of different signal dimensions, including the primary signal dimension and the at least one secondary signal dimension. This may improve the efficiency and/or accuracy of signal representation determination compared to independently processing signals of different signal dimensions.

Figure 1:
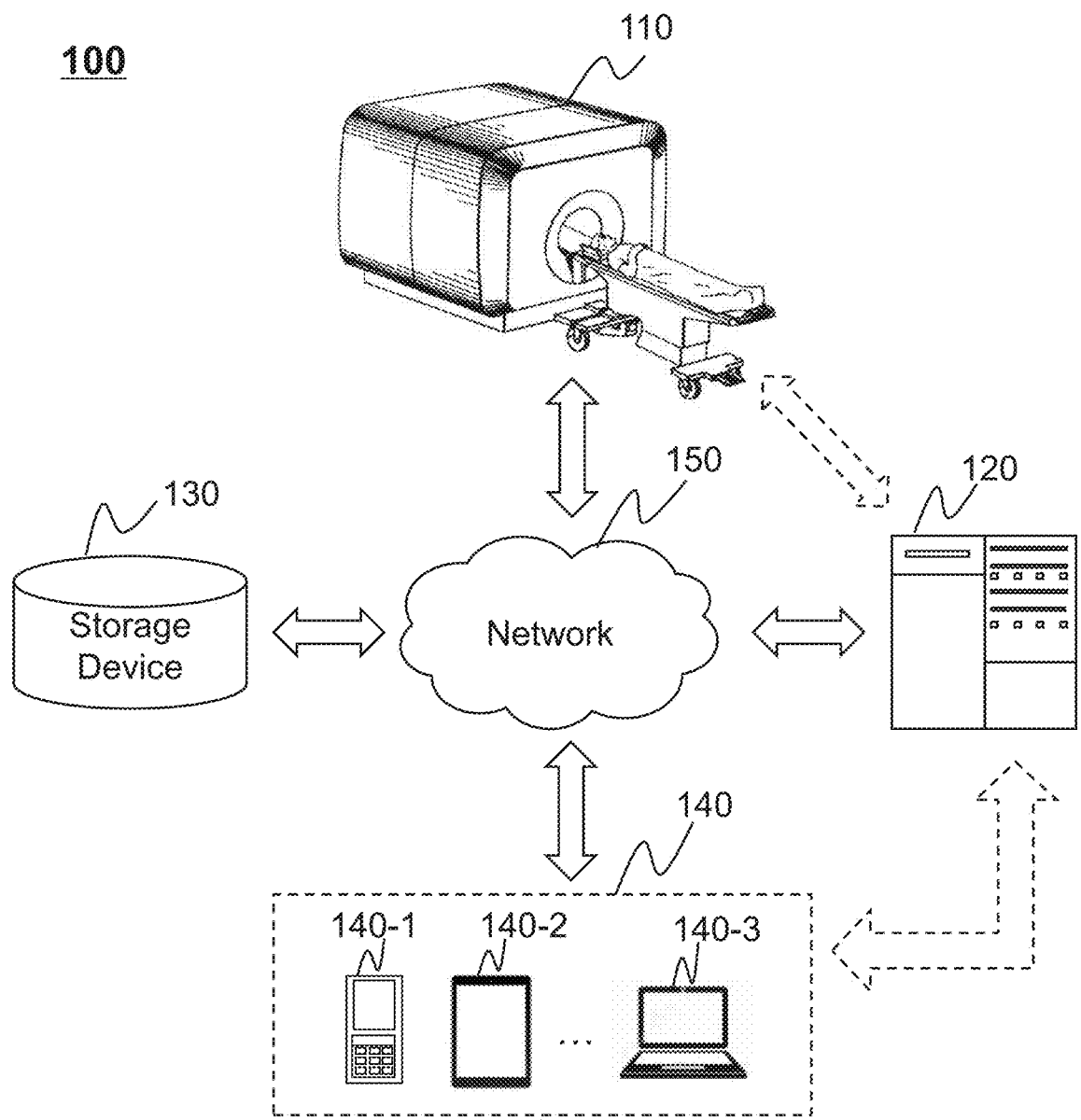
FIG. 1 is a schematic diagram illustrating an exemplary MRI system according to some embodiments of the present disclosure.

FIG. 1 is a schematic diagram illustrating an exemplary MRI system 100 according to some embodiments of the present disclosure. As shown in FIG. 1, the MRI system 100 may include an MR scanner 110, a processing device 120, a storage device 130, one or more terminals 140, and a network 150. In some embodiments, the MR scanner 110, the processing device 120, the storage device 130, and/or the terminal(s) 140 may be connected to and/or communicate with each other via a wireless connection, a wired connection, or a combination thereof. The connections between the components in the MRI system 100 may be variable. For example, the MR scanner 110 may be connected to the processing device 120 through the network 150. As another example, the MR scanner 110 may be connected to the processing device 120 directly.

The MR scanner 110 may be configured to scan a subject (or a part of the subject) to acquire image data, such as echo signals (or MR signals) associated with the subject. For example, the MR scanner 110 may detect a plurality of echo signals by applying an MR pulse sequence on the subject. In some embodiments, the MR scanner 110 may include, for example, a magnetic body, a gradient coil, an RF coil, etc., as described in connection with FIG. 2. In some embodiments, the MR scanner 110 may be a permanent magnet MR scanner, a superconducting electromagnet MR scanner, or a resistive electromagnet MR scanner, etc., according to types of the magnetic body. In some embodiments, the MR scanner 110 may be a high-field MR scanner, a mid-field MR scanner, and a low-field MR scanner, etc., according to the intensity of the magnetic field.

The subject may be biological or non-biological. For example, the subject may include a patient, a man-made object, etc. As another example, the subject may include a specific portion, organ, tissue, and/or a physical point of the patient. For example, the subject may include head, brain, neck, body, shoulder, arm, thorax, cardiac, stomach, blood vessel, soft tissue, knee, feet, or the like, or a combination thereof.

The processing device 120 may process data and/or information obtained from the MR scanner 110, the storage device 130, and/or the terminal(s) 140. For example, the processing device 120 may generate an MR image by processing image data (e.g., echo signals) collected by the MR scanner 110. As another example, the processing device 120 may determine a signal representation of the subject based on the image data (e.g., echo signals) of the subject collected by the MR scanner 110. Optionally, the processing device 120 may further determine a value of a quantitative parameter (also referred to as a quantitative parameter of interest herein) of the subject based on the signal representation. In some embodiments, the processing device 120 may be a single server or a server group. The server group may be centralized or distributed. In some embodiments, the processing device 120 may be local or remote. For example, the processing device 120 may access information and/or data from the MR scanner 110, the storage device 130, and/or the terminal(s) 140 via the network 150. As another example, the processing device 120 may be directly connected to the MR scanner 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 300 having one or more components as described in connection with FIG. 3.

The storage device 130 may store data, instructions, and/or any other information. In some embodiments, the storage device 130 may store data obtained from the MR scanner 110, the processing device 120, and/or the terminal(s) 140. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or a combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the MRI system 100 (e.g., the MR scanner 110, the processing device 120, and/or the terminal(s) 140). One or more components of the MRI system 100 may access the data or instructions stored in the storage device 130 via the network 150. In some embodiments, the storage device 130 may be part of the processing device 120 or the terminal(s) 140.

The terminal(s) 140 may be configured to enable a user interaction between a user and the MRI system 100. For example, the terminal(s) 140 may receive an instruction to cause the MR scanner 110 to scan the subject from the user. As another example, the terminal(s) 140 may receive a processing result (e.g., a signal representation or a value of a quantitative parameter of the subject) from the processing device 120 and display the processing result to the user. In some embodiments, the terminal(s) 140 may be connected to and/or communicate with the MR scanner 110, the processing device 120, and/or the storage device 130. In some embodiments, the terminal(s) 140 may include a mobile device 140-1, a tablet computer 140-2, a laptop computer 140-3, or the like, or a combination thereof. For example, the mobile device 140-1 may include a mobile phone, a personal digital assistant (PDA), a gaming device, a navigation device, a point of sale (POS) device, a laptop, a tablet computer, a desktop, or the like, or a combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120 or the MR scanner 110.

The network 150 may include any suitable network that can facilitate the exchange of information and/or data for the MRI system 100. In some embodiments, one or more components of the MRI system 100 (e.g., the MR scanner 110, the processing device 120, the storage device 130, the terminal(s) 140, etc.) may communicate information and/or data with one or more other components of the MRI system 100 via the network 150. For example, the processing device 120 may obtain image data (e.g., an echo signal) from the MR scanner 110 via the network 150. As another example, the processing device 120 may obtain user instructions from the terminal(s) 140 via the network 150. The network 150 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, or the like, or a combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 150 may include one or more network access points. For example, the network 150 may include wired and/or wireless network access points such as base stations and/or Internet exchange points through which one or more components of the MRI system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the storage device 130 may be a data storage including cloud computing platforms, such as a public cloud, a private cloud, a community and hybrid cloud, etc. In some embodiments, the processing device 120 may be integrated into the MR scanner 110. However, those variations and modifications do not depart the scope of the present disclosure.

Figure 2:
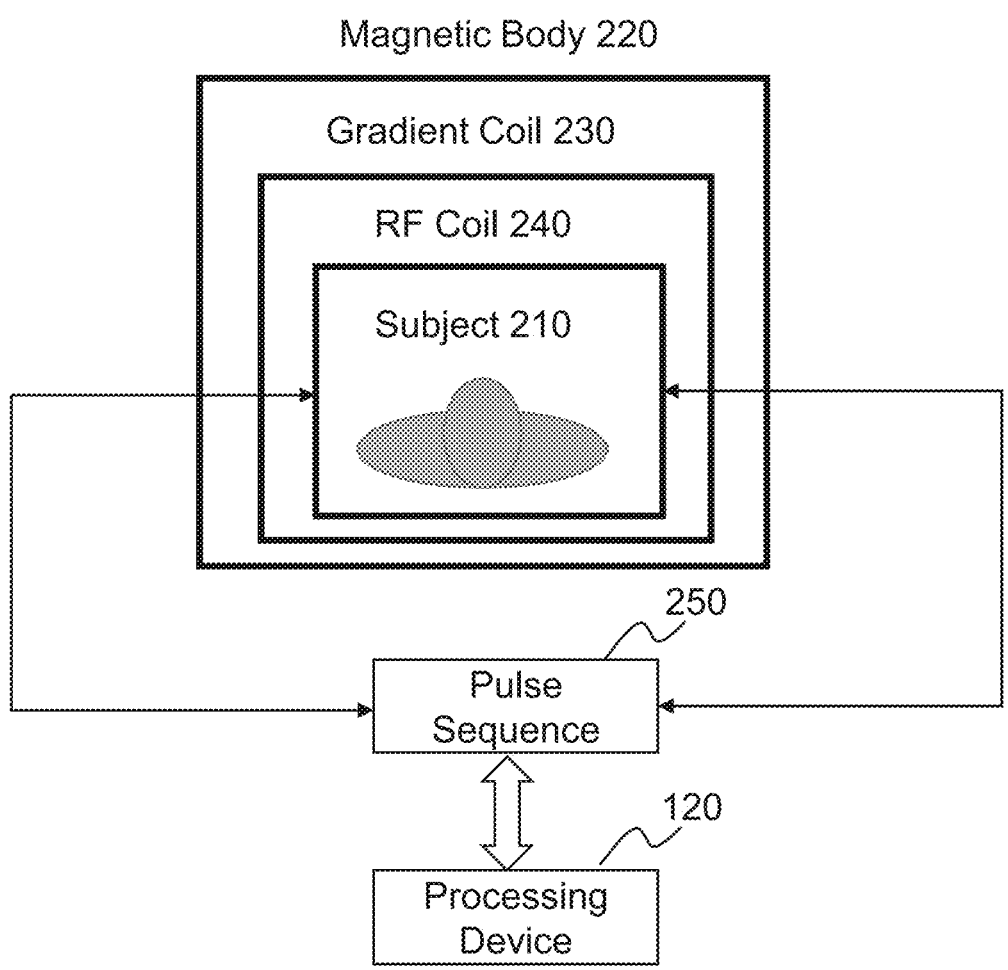
FIG. 2 is a block diagram illustrating an exemplary MR scanner according to some embodiments of the present disclosure.

FIG. 2 is a block diagram illustrating an exemplary MR scanner 110 according to some embodiments of the present disclosure. As illustrated in FIG. 2, the MR scanner 110 may include a magnetic body 220, a gradient coil 230, an RF coil 240, and a pulse sequence module 250.

The magnetic body 220 may generate a static magnetic field during the scanning of at least a portion of a subject 210. The magnetic body 220 may be of various types including, for example, a permanent magnet, a superconducting electromagnet, a resistive electromagnet, etc.

The gradient coil 230 may provide magnetic field gradients to the main magnetic field in an X direction, a Y direction, and/or a Z direction. As used herein, the X direction, the Y direction, and the Z direction may represent an X axis, a Y axis, and a Z axis in a coordinate system. For example, the Z axis may be along the axis of the magnetic body 220, the X axis and the Z axis may form a horizontal plane, and the X axis and the Y axis may form a vertical plane. In some embodiments, the gradient coil 230 may include an X-direction coil for providing a magnetic field gradient to the main magnetic field in the X direction, a Y-direction coil for providing a magnetic field gradient to the main magnetic field in the Y direction, and/or Z-direction coil for providing a magnetic field gradient to the main magnetic field in the Z direction. In some embodiments, the X-direction coil, the Y-direction coil, and/or the Z-direction coil may be of various shape or configuration. For example, the Z-direction coil may be designed based on a circular (Maxwell) coil. As another example, the X-direction coil and the Y-direction coil may be designed on the basis of a saddle (Golay) coil configuration.

The RF coil 240 may emit RF pulse signals to and/or receive echo signals from the subject 210 being examined. In some embodiments, the RF coil 240 may include a transmitting coil and a receiving coil. The transmitting coil may emit signals (e.g., RF pulses) that may excite a nucleus in the subject 210 to provide a resonation. The receiving coil may receive echo signals emitted from the subject 210. In some embodiments, the RF transmitting coil and RF receiving coil may be integrated into one same coil. In some embodiments, the RF coil 240 may be of various types including, for example, a quadrature detection (QD) orthogonal coil, a phased-array coil, a specific element spectrum coil, etc. In some embodiments, the RF coil 240 may be a phased-array coil that includes multiple coil units (also referred to as RF receiving coil units herein), each of which may detect echo signals independently.

In some embodiments, the RF coil 240 may be used to detect signals generated by an MR pulse sequence (also referred to as an MRI protocol herein). The MR pulse sequence may be of various types, such as a spin echo (SE) pulse sequence, a gradient refocused echo (GRE) pulse sequence, an inversion recovery (IR) pulse sequence, a multi-echo MR pulse sequence, a T1ρ-prepared pulse sequence, a T2-prepared pulse sequence, a diffusion weighted imaging (DWI) pulse sequence, etc. As used herein, the multi-echo MR pulse sequence may refer to a pulse sequence in which a plurality of signals of a plurality of echoes are produced (or detected) after every excitation pulse. The T1ρ-prepared pulse sequence may refer to a pulse sequence that includes a T1ρ weighted magnetization preparation pulse (also referred to as a spin-lock pulse). The T2-prepared pulse sequence may refer to a pulse sequence that includes a T2 preparation pulse. The DWI pulse sequence may refer to a pulse sequence (normally a spin echo sequence) having a pair of diffusion-sensitizing gradients applied before and after, e.g., a 180-degree pulse in the pulse sequence.

In some embodiments, the MR pulse sequence may be defined by one or more parameters including, for example, the type of the MR pulse sequence, a time for applying the MR pulse sequence, a duration of the MR pulse sequence, relating to an RF pulse in the MR pulse sequence, a count (or number) of RF pulses in the MR pulse sequence, a unit repetition time (TR), a repetition count, an inversion time (TI), a b-value, a T1ρ-preparation duration, a T2-preparation duration, an echo train length, an echo spacing, a velocity encoding (VENC) value, a count (or number) of averages, etc. As used herein, the TR may refer to the timespan between two repeating and consecutive RF pluses in an MR pulse sequence (e.g., the timespan between two consecutive excitation RF pulses in an SE pulse sequence, the timespan between two consecutive 180° inversion pulses in an IR pulse sequence). The repetition count may refer to the count (or number) of repetitions in an MR pulse sequence. The TI may refer to the timespan between a 180° inversion pulse and a following 90° excitation pulse in an IR pulse sequence. The b-value may refer to a factor that reflects the strength and timing of diffusion-sensitizing gradients in a DWI pulse sequence. The T1ρ-preparation duration may refer to the duration of a spin-lock pulse in a T1ρ-prepared pulse sequence. The T2-preparation duration may refer to the duration of a T2 preparation pulse in a T2-prepared pulse sequence.

In some embodiments, the RF coil 240 may detect (or receive) one or more echo signals corresponding to one or more echoes excited by the MR pulse sequence. In some embodiments, an echo signal (or an echo) may be defined by one or more parameters, for example, an echo signal type (a spin echo, a fast spin echo (FSE), a fast recovery FSE, a single shot FSE, a gradient recalled echo, a fast imaging with steady-state precession), an echo time (TE), an echo signal intensity, a coil unit (e.g., denoted by an identification (ID) or a serial number of the coil unit) that detects the echo signal, a repetition (e.g., denoted by a repetition serial number) in which the echo signal is detected, etc. The TE may refer to the time between an application of an excitation RF pulse and the peak of an echo excited by the excitation RF pulse.

The pulse sequence module 250 may be configured to define parameters and arrangements relating to the MR scanner 110 before and/or during the scan of the subject 210. In some embodiments, the parameters relating to the MR scanner 110 may include one or more parameters relating to an MR pulse sequence (e.g., the type of the MR pulse sequence, a TR, a repetition count, a TI, etc.) applied by the MR scanner 110, one or more parameters relating to a gradient field generated by the gradients coil 230 or a radiofrequency field (e.g. an RF center frequency, a flip angle), one or more parameters relating to echo signals (e.g., a TE, a spin echo type) detected by the RF coil 240 as described elsewhere in the disclosure, or the like, or any combination thereof. In some embodiments, the parameters relating to the MR scanner 110 may include one or more other imaging parameters, such as, a count (or number) of RF channels, an image contrast and/or ratio, a slice thickness, an imaging type (e.g., a T1 weighted imaging, a T2 weighted imaging, a proton density weighted imaging, etc.), a field of view (FOV) of the MR scanner 110, an off center frequency shift of the MR scanner 110, or the like, or a combination thereof.

In some embodiments, the pulse sequence module 250 may be connected to and/or communicate with the processing device 120. For example, before an MRI scanning process, at least one portion of the parameters and arrangements relating to the MR scanner 110 may be designed and/or determined by the processing device 120 according to clinical demands or a scanning protocol, and transmitted to the pulse sequence module 250. In an MR scanning process, the MR scanner 110 may scan the subject 210 based on the parameters and arrangements defined by the pulse sequence module 250. For example, the MR scanner 110 may apply an MR pulse sequence with specific parameters relating to MR pulse sequences defined by the pulse sequence module 250, and the RF coil 240 may receive echo signals according to specific parameters relating to echo signals defined by the pulse sequence module 250. In some embodiments, an echo signal and data generated based on the echo signal (e.g., image data or K-space data) may be defined by the parameters relating to the MR scanner 110 under which the echo signal is acquired using the MR scanner 110. For example, the parameters relating to the MR scanner 110 under which the echo signal is acquired may be regarded as a plurality of signal dimension of the echo signal and the data generated based on the echo signal. More descriptions regarding the signal dimensions may be found elsewhere in the present disclosure. See, e.g., FIG. 6 and relevant descriptions thereof.

This description regarding the MR scanner 110 provided above is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the pulse sequence module 250 may be integrated into the processing device 120. However, those variations and modifications do not depart the scope of the present disclosure.

FIG. 3 is a schematic diagram illustrating exemplary hardware and/or software components of a computing device 300 according to some embodiments of the present disclosure. In some embodiments, one or more components of the MRI system 100 may be implemented on one or more components of the computing device 300. Merely by way of example, the processing device 120 and/or the terminal(s) 140 may be implemented one or more components of the computing device 300, respectively.

As illustrated in FIG. 3, the computing device 300 may include a processor 310, a storage 320, an input/output (I/O) 330, and a communication port 340. The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process image data of a subject obtained from the MR scanner 110, the storage device 130, terminal(s) 140, and/or any other component of the MRI system 100. In some embodiments, the processor 310 may determine a signal representation and/or a value of a quantitative parameter of a subject based on image data of the subject acquired by the MR scanner 110.

In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 300. However, it should be noted that the computing device 300 in the present disclosure may also include multiple processors. Thus operations and/or method steps that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the MR scanner 110, the storage device 130, the terminal(s) 140, and/or any other component of the MRI system 100. In some embodiments, the storage 320 may include a mass storage device, a removable storage device, a volatile read-and-write memory, a read-only memory (ROM), or the like, or a combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 120 for determining a signal representation.

The I/O 330 may input and/or output signals, data, information, etc. In some embodiments, the I/O 330 may enable a user interaction with the computing device 300 (e.g., the processing device 120). In some embodiments, the I/O 330 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 340 may be connected to a network (e.g., the network 150) to facilitate data communications. The communication port 340 may establish connections between the computing device 300 (e.g., the processing device 120) and one or more components of the MRI system 100 (e.g., the MR scanner 110, the storage device 130, and/or the terminal(s) 140). The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
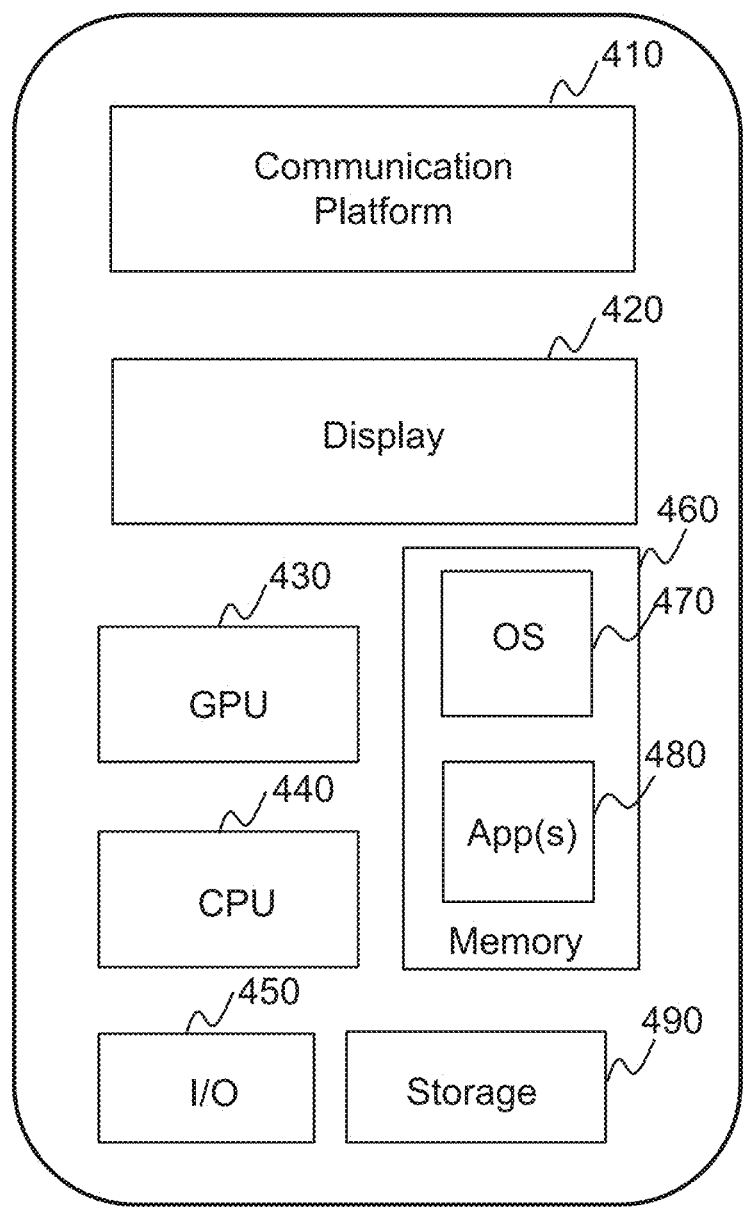
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device 400 may be implemented according to some embodiments of the present disclosure. In some embodiments, one or more components of the MRI system 100 may be implemented on one or more components of the mobile device 400. Merely by way of example, a terminal 140 may be implemented on one or more components of the mobile device 400.

As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 120. User interactions with the information stream may be achieved via the I/O 450 and provided to the processing device 120 and/or other components of the MRI system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5:
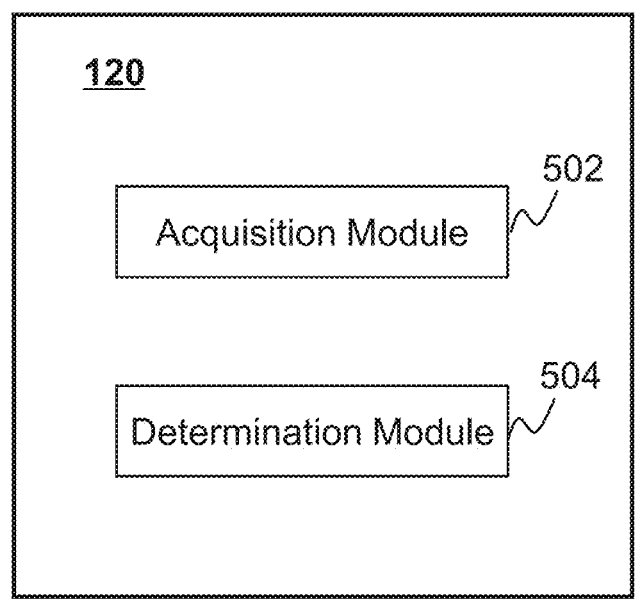
FIG. 5 is a block diagram illustrating an exemplary processing device according to some embodiments of the present disclosure.
Figure 8A:
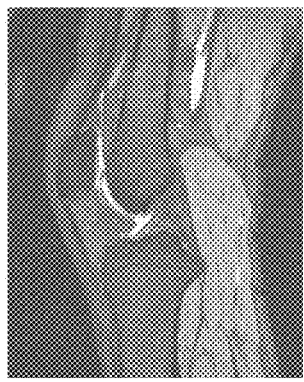
FIGS. 8A to 8E are schematic diagrams illustrating exemplary T2*-quantitative maps of a knee of a patient according to some embodiments of the present disclosure.
Figure 8B:
Figure 8C:
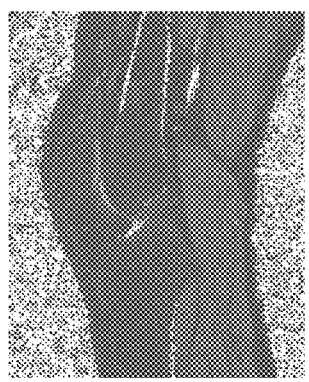
Figure 8D:
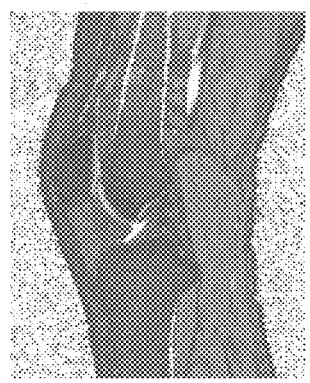
Figure 8E:
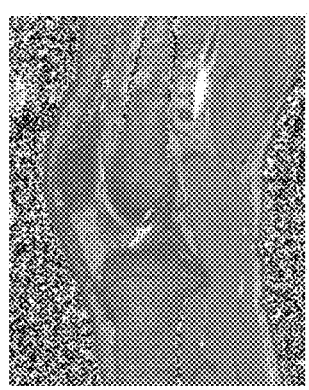

FIG. 5 is a block diagram illustrating an exemplary processing device 120 according to some embodiments of the present disclosure. As shown in FIG. 5, the processing device 120 may include an acquisition module 502 and a determination module 504.

The acquisition module 502 may be configured to acquire information related to the MRI system 100. For example, the acquisition module 502 may acquire a plurality of signals of the subject. The plurality of signals may be generated using an MRI device (e.g., the MR scanner 110). As used herein, a signal of the subject may convey information about one or more attributes or characteristics of the subject. For example, the signals of the subject may be or include image data or K-space data relating to the subject. In some embodiments, each of the signals of the subject may correspond to a set of values in a plurality of signal dimensions of signal acquisition using the MRI device. As another example, the acquisition module 502 may acquire an optimization function for determining a signal representation of the subject based on the plurality of signals of the subject.

The determination module 504 may be configured to determine a primary signal dimension and at least one secondary signal dimension among the plurality of signal dimensions. The primary signal dimension may refer to a signal dimension of the signals of the subject that is associated with the signal representation. The at least one secondary signal dimension may include any signal dimension of the signals of the subject other than the primary signal dimension. More descriptions regarding the determination of the primary signal dimension and the at least one secondary signal dimension may be found elsewhere in the present disclosure. See, e.g., operation 604 and relevant descriptions thereof.

The determination module 504 may also be configured to determine the signal representation of the subject based on the plurality of signals, the primary signal dimension, and the at least one secondary signal dimension. More descriptions regarding the determination of the signal representation of the subject may be found elsewhere in the present disclosure. See, e.g., operation 606 and relevant descriptions thereof. Optionally, the determination module 504 may determine a value of a quantitative parameter of the subject based on the signal representation of the subject. Exemplary quantitative parameters of the subject may include a longitudinal relaxation time, a transverse relaxation time, an apparent diffusion coefficient (ADC), a transverse relaxation decay, a field distribution, a longitudinal relaxation time in a rotating frame, or the like, or any combination thereof. More descriptions regarding the determination of the value of the quantitative parameter of the subject may be found elsewhere in the present disclosure. See, e.g., operation 608 and relevant descriptions thereof.

In some embodiments, the modules may be hardware circuits of all or part of the processing device 120. The modules may also be implemented as an application or set of instructions read and executed by the processing device 120. Further, the modules may be any combination of the hardware circuits and the application/instructions. For example, the modules may be the part of the processing device 120 when the processing device 120 is executing the application/set of instructions.

It should be noted that the above description of the processing device 120 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120 may further include one or more additional modules, such as a storage module. Additionally or alternatively, one or more of the modules described above may be omitted. In addition, any module mentioned above may be implemented in two or more separate units. For example, the determination module 504 may be divided into a first unit configured to determine the primary signal dimension and the secondary signal dimension, a second unit configured to determine the signal representation of the subject, and a third unit configured to determine the value of the quantitative parameter of the subject.

FIG. 6 is a flowchart illustrating an exemplary process for determining a signal representation of a subject according to some embodiments of the present disclosure. In some embodiments, one or more operations of process 600 may be implemented in the MRI system 100 illustrated in FIG. 1. For example, the process 600 may be stored in a storage device (e.g., the storage device 130, the storage 320, and/or the storage 490) of the MRI system 100 in the form of instructions, and invoked and/or executed by the processing device 120 (e.g., the processor 310 of the computing device 300 as illustrated in FIG. 3, the CPU 440 of the mobile device 400 as illustrated in FIG. 4, one or more modules as illustrated in FIG. 5).

As used herein, the subject may refer to any biological or non-biological subject, such as a patient (or a portion of the patient), a man-made object (e.g., a phantom). In some embodiments, the subject may refer to a physical point of an object (e.g., a patient, an organ or tissue of the patient, an animal). For illustration purposes, a patient is described as an exemplary object in the following descriptions. In some embodiments, the MR scanner 110 may be used to scan the subject (or the patient that includes the subject) to acquire one or more echo signals from the subject (or the patient that includes the subject). As used herein, the signal representation may refer to a representative value or an attribute value of the echo signals. The signal representation of the subject may reflect one or more physiological characteristics or physical characteristics of the subject, which may provide a basis for medical diagnosis and/or treatment. More descriptions regarding the signal representation may be found elsewhere in the present disclosure. See, e.g., operations 604 to 608 and relevant descriptions thereof.

In 602, the processing device 120 (e.g., the acquisition module 502) may acquire a plurality of signals of the subject. The plurality of signals may be generated using an MRI device (e.g., the MR scanner 110), for example, by applying a multi-echo pulse sequence on the subject. As used herein, a signal of the subject may convey information about one or more attributes or characteristics of the subject. For example, the signals of the subject may be or include image data or K-space data relating to the subject.

In some embodiments, the processing device 120 may cause the MRI device to apply an MR pulse sequence (e.g., an SE pulse sequence, a GRE pulse sequence, an IR pulse sequence, a multi-echo pulse sequence, a T1ρ-prepared pulse sequence, a T2-prepared pulse sequence, a DWI pulse sequence as described elsewhere in this disclosure) to scan the subject. In some embodiments, the subject may be a physical point of a patient. The processing device 120 may cause the MRI device to apply the MR pulse sequence on the patient. The MRI device may include a plurality of coil units, which may detect a plurality of echo signals excited by the MR pulse sequence during the scan.

The processing device 120 may further determine the plurality of signals based on the echo signals detected by the coil units. For example, the processing device 120 may fill the echo signals into a plurality of regions of the K-space (e.g., a k-space matrix) to generate a plurality of sets of k-space data, wherein the plurality of sets of k-space data may be designated as the signals of the subject. As another example, the subject may be a physical point of a patient. The processing device 120 may reconstruct a plurality of images based on the plurality of echo signals, wherein each image may include image data (e.g., a pixel having a specific pixel value, a voxel having a specific voxel value) of the physical point. The processing device 120 may then designate the image data of the physical point in the images as the signals of the physical point. As yet another example, the echo signals may form a plurality of echo trains based on a trajectory of k-space, wherein the plurality of echo trains may be designated as the signals of the subject.

In some embodiments, the echo signals may be complex signals or real number signals, and the signals of the subject determined based on the echo signals may have complex numbers or real numbers. Merely by way of example, the subject may be a physical point of a patient. Each of the reconstructed images may include a complex pixel value or a real number pixel value of a pixel corresponding to the physical point. The complex pixel value or the real number pixel value of the physical point in each image may be designated as one of the signals of the subject.

In some embodiments, the plurality of signals of the subject may be previously determined by the processing device 120 or another computing device, and stored in a storage device of the MRI system 100 (e.g., the storage device 130) or an external source. The processing device 120 may acquire the signals from the storage device 130 or the external source.

In some embodiments, each of the signals of the subject may correspond to a set of values in a plurality of signal dimensions of signal acquisition using the MRI device. As used herein, a signal dimension of a signal may refer to a parameter that describes an instance under which the signal is determined or acquired using the MRI device. Merely by way of example, a signal A of the subject may be a pixel value of a physical point in an image, wherein the image may be reconstructed based on an echo signal detected by the MRI device during a scan of the subject. The signal dimensions corresponding to the signal A may include, for example, one or more parameters relating to the MRI device during the scan of the subject, one or more parameters relating to the determination of the signal A based on the corresponding image (e.g., a coordinate of a corresponding pixel in the image), etc. Exemplary parameters relating to the MRI device during the scan may include one or more parameters relating to the MR pulse sequence (e.g., a TE, a TR, a TI, a b-value, a T1ρ-preparation duration, a T2-preparation duration, a velocity encoding value, a repetition) applied during the scan, one or more parameters relating to a gradient field or radiofrequency field (e.g. an RF center frequency, a flip angle) applied during the scan, one or more other imaging parameters (e.g., a count (or number) of RF channels, a coil unit) of the MRI device, or the like, or any combination thereof. More descriptions regarding the parameters relating to the MRI device during the scan of the subject may be found elsewhere in the present disclosure. See, e.g., FIG. 2 and relevant descriptions thereof.

For illustration purposes, an example of a plurality of signals of a physical point $P_r$ of a patient is provided in Table 1 as below. The signals of $P_r$ may be acquired using an MRI device having m coil units. The MRI device may be caused to apply a multi-echo pulse sequence including 2 repetitions on the patient. In each repetition, each coil unit may detect n echo signals corresponding to n echoes sequentially occurred at different TEs (denoted as $TE_1$, $TE_2$, ..., and $TE_n$). In some embodiments, the plurality of echoes may sequentially occur at a substantially same time interval (denoted as $\Delta TE$) between successive echoes. The echo signals detected by each coil unit may be used to reconstruct a series of images, each of which may include a pixel value of a pixel corresponding to a physical point $P_r$ (referred to as the pixel value of $P_r$ for brevity). The pixel values of $P_r$ in the images may be designated as the signals of $P_r$. In some embodiments, a pixel value of $S_r$ in an image may reflect a signal intensity of MRI signals of the physical point $S_r$.

TABLE 1

An example of a plurality of signals of a physical point $P_r$

| Repetition$_1$ | | Repetition$_2$ | |
|---|---|---|---|
| Coil$_1$ ... Coil$_m$ | | Coil$_1$ ... Coil$_m$ | |
| $S_{e_1}^1(r)$ ... $S_{e_1}^m(r)$ | | $S_{e_1}^{1'}(r)$ ... $S_{e_1}^{m'}(r)$ | |
| $S_{e_2}^1(r)$ ... $S_{e_2}^m(r)$ | | $S_{e_2}^{1'}(r)$ ... $S_{e_2}^{m'}(r)$ | |
| ... ... ... | | ... ... ... | |
| $S_{e_n}^1(r)$ ... $S_{e_n}^m(r)$ | | $S_{e_n}^{1'}(r)$ ... $S_{e_n}^{m'}(r)$ | | where $S_{e_1}^1(r)$ to $S_{e_n}^m(r)$ refer to the plurality of signals of $P_r$, $S_{e_n}^m(r)$ refers a pixel value of $P_r$ in an image that is reconstructed based on the $n^{th}$ echo signal detected by the $m^{th}$ coil unit in Repetition$_1$, and $S_{e_n}^{m'}$ refers a pixel value of $P_r$ in an image that is reconstructed based on the $n^{th}$ echo signal detected by the $m^{th}$ coil unit in Repetition$_2$.

Each signal of $P_r$ in Table 1 may correspond to a set of values in a plurality of signal dimensions of signal acquisition using the MRI device. Exemplary signal dimensions may include an echo time, a coil unit, a repetition, or the like, or any combination thereof. For example, the $S_{e_n}^m(r)$ may correspond to $TE_n$ in the echo time, in in the coil unit, and 1 in the repetition. It should be noted that the above example illustrated in Table 1 is merely provided for the purposes of illustration, and not intended to limit the scope of the present disclosure. For example, the multi-echo pulse sequence applied on the patient may include only one repetition and/or more than one flip angle.

In 604, the processing device 120 (e.g., the determination module 504) may determine a primary signal dimension and at least one secondary signal dimension among the plurality of signal dimensions.

As used herein, the primary signal dimension may refer to a signal dimension of the signals of the subject that is associated with the signal representation. A signal dimension may be regarded as being associated with the signal representation if the signal dimension and the signal representation have a certain mathematical correlation (e.g., an index correlation, a linear correlation, or any other mathematical correlation). For illustration purposes, the $P_r$ is described as an exemplary subject and exemplary primary signal dimensions of the signals of $P_r$ is provided hereinafter. Referring back to the example in Table 1, the MRI device may be caused to scan the patient using the multi-echo pulse sequence. The signal representation of $P_r$ may be a change of signal intensity at $P_r$ over the time interval $\Delta TE$ between successive echoes, which is denoted as $\Delta S1(r)$. As used herein, a signal intensity at $P_r$ may refer to an intensity or strength of MRI signals of the $P_r$. In some embodiments, the signal representation ΔS1(r) may be associated with the echo time as illustrated in Equation (1) or Equation (2) as below:

$$\Delta S1(r)=e^{-\Delta TE/T^*_2(r)+i\gamma\Delta B(r)\Delta TE}, \quad (1)$$

and $$\Delta S1(r)=e^{-\Delta TE/T_2(r)}, \quad (2)$$

where $T^*_2(r)$ refers to a transverse relaxation decay of $P_r$, $\gamma$ refers to a gyromagnetic ratio, $\Delta B(r)$ refers to a local field distribution at $P_r$, and $T_2(r)$ refers to a transverse relaxation time of $P_r$. In this case, the primary signal dimension may be the echo time that is associated with $\Delta S1(r)$.

As another example, the MRI device may be caused to scan the patient using a T2-prepared pulse sequence, which includes a plurality of T2 preparation pulses with different T2-preparation durations. The signal representation of $P_r$ may be a change of signal intensity at $P_r$ over a time interval $\Delta\partial$, which is denoted as ΔS2. $\Delta\partial$ may refer to a time difference between two T2-preparation durations corresponding to two successive T2 preparation pulses in the T2-prepared pulse sequence. The signal representation ΔS2 may be associated with T2-preparation duration as illustrated in Equation (3) as below:

$$\Delta S2(r)=e^{-\Delta\partial/T_2(r)}, \quad (3)$$

where $T_2(r)$ refers to a transverse relaxation time of $P_r$. In this case, the primary signal dimension may be the T2-preparation duration that is associated with ΔS2(r).

As yet another example, the MRI device may be caused to scan the patient using a T1ρ-prepared pulse sequence, which includes a plurality of T1ρ weighted magnetization preparation pulses with different T1ρ-preparation durations. The signal representation of $P_r$ may be a change of signal intensity at $P_r$ over a time interval Δτ, which may be denoted as ΔS3. Δτ may refer to a time difference between two T1ρ-preparation durations corresponding to two successive T1ρ weighted magnetization preparation pulses in the T1ρ-prepared pulse sequence. The signal representation ΔS3 may be associated with the T1ρ-preparation duration as illustrated in Equation (4) as below:

$$\Delta S3(r)=e^{-\Delta\tau/T_1\rho(r)}, \quad (4)$$

where $T_1\rho(r)$ refers to a longitudinal relaxation time in a rotating frame of $P_r$. In this case, the primary signal dimension may be the T1ρ-preparation duration that is associated with ΔS3(r).

As yet another example, the MRI device may be caused to scan the patient using an IR pulse sequence, which includes a plurality of excitation pulses at different TIs. The signal representation of $P_r$ may be a change of signal intensity at $P_r$ over ΔTI, which is denoted as ΔS4(r). ΔTI may refer to a time difference between two TIs corresponding to two successive excitation pulses in the IR pulse sequence. In some embodiments, the signal representation ΔS4(r) may be associated with the inversion time as illustrated in Equation (5) as below:

$$\Delta S4(r)=e^{-\Delta TI/T_1(r)}, \quad (5)$$

where $T_1(r)$ refers a longitudinal relaxation time of $P_r$. In this case, the primary signal dimension may be the inversion time that is associated with ΔS4(r).

As yet another example, the MRI device may be caused to apply a DWI pulse sequence on the patient, which includes a plurality of pairs of diffusion-sensitizing gradients with different b-values. The signal representation of $P_r$ may be a change of signal intensity at $P_r$ with Δb, which is denoted as ΔS5. Δb may refer to a difference between two b-values corresponding to two successive pairs of diffusion-sensitizing gradients in the DWI pulse sequence. The signal representation ΔS5 may be associated with the b-value as illustrated in Equation (6) as below:

$$\Delta S5(r)=e^{-\Delta b/ADC(r)}, \quad (6)$$

where ADC(r) refers an apparent diffusion coefficient (ADC) of $P_r$. In this case, the primary signal dimension may be the b-value that is associated with ΔS5(r).

The at least one secondary signal dimension may include any signal dimension of the signals of the subject other than the primary signal dimension. In some embodiments, each of the secondary signal dimension may be not associated (or correlate) with the signal representation. In some embodiments, the at least one secondary signal dimension may include all or a portion of the signal dimension(s) of the signals of the subject other than the primary signal dimension. In some embodiments, a signal dimension may be determined as a secondary signal dimension if it is not associated with the signal representation and has two or more values in the signal dimension. For example, referring back to the example in Table 1, the at least one secondary signal dimension may include two secondary signal dimensions, the dimension of coil unit and the dimension of repetition, which is not associated with the ΔS1(r) according to Equation (1) as described above. If the multi-echo pulse sequence applied on the patient includes only one repetition (i.e., there is only one value in the repetition), the repetition may not be designated as a secondary signal dimension.

In some embodiments, two or more signal dimensions of the plurality of signal dimensions may be associated with the signal representation. One of the two or more signal dimensions may be selected as the primary signal dimension. The selection may be performed by the processing device 120 autonomously or based on a user instruction. The unselected signal dimension(s) associated with the signal representation may be designated as one or more secondary signal dimensions or be omitted from processing.

In 606, the processing device 120 (e.g., the determination module 504) may determine the signal representation of the subject based on the plurality of signals, the primary signal dimension, and the at least one secondary signal dimension.

In some embodiments, the processing device 120 may determine the signal representation of the subject by performing one or more operations in process 700A as described in connection with FIG. 7A. Alternatively, the processing device 120 may determine the signal representation of the subject based on an optimization function of the signal representation by performing one or more operations in process 700B as described in connection with FIG. 7B. In some embodiments, the signal representation of the subject may be represented by a complex number or a real number value. In some embodiments, the signal representation of the subject may be described in the form of a function, such as any of the Equation (1) to Equation (6).

In some embodiments, the subject may be a physical point of a patient as described above. The patient may include one or more other physical points. For each physical point of the patient, operations 602 to 606 may be performed to determine a signal representation of the physical point. The signal representations of the physical points of the patient may reflect one or more physiological or physical characteristics of different portions of the patient, and thereby can be used in disease diagnoses. In some embodiments, the processing device 120 may generate an image including a plurality of pixels corresponding to the physical points of the patient, wherein the pixel values of the pixels may be determined based on the signal representations of the corresponding physical points. The image may intuitively reflect the signal representations of different physical points of the patient and serve as a basis of disease diagnosis.

In some embodiments, the process 600 may further include an additional operation 608. In 608, the processing device 120 (e.g., the determination module 504) may determine a value of a quantitative parameter of the subject based on the signal representation of the subject.

In some embodiments, the signal representation of the subject may be associated with the quantitative parameter. The primary signal dimension may be associated with the quantitative parameter. Each of the at least one secondary signal dimension may be not associated with the quantitative parameter. In some embodiments, a quantitative parameter may be regarded as being associated with a signal dimension if the quantitative parameter and the signal dimension have a certain correlation, e.g., a correlation that may be presented or described using a mathematical relationship (e.g., an index correlation, a linear correlation, or any other mathematical correlation).

For illustration purposes, the physical point $P_r$ of the patient is described as an exemplary subject and a determination of exemplary quantitative parameters of $P_r$ is provided hereinafter. For example, the signal representation of $P_r$ may be $\Delta S1(r)$ and the quantitative parameter may include $T^*_2(r)$ and/or $\Delta B(r)$, wherein both $T^*_2(r)$ and $\Delta B(r)$ are associated with the echo time (i.e., the primary signal dimension with respect to $\Delta S1(r)$) according to Equation (1). As another example, the signal representation of $P_r$ may be $\Delta S2(r)$ and the quantitative parameter may be $T_2(r)$, wherein $T_2(r)$ is associated with the T2-preparation duration (i.e., the primary signal dimension with respect to $\Delta S2(r)$ according to Equation (3). As yet another example, the signal representation of $P_r$ may be $\Delta S3(r)$ and the quantitative parameter may be $T_{1\rho}(r)$, wherein $T_{1\rho}(r)$ is associated with the T1ρ-preparation duration (i.e., the primary signal dimension with respect to $\Delta S3(r)$) according to Equation (4). As yet another example, the signal representation of $P_r$ may be $\Delta S4(r)$ and the quantitative parameter may be $T_1(r)$, wherein $T_1(r)$ is associated with the inversion time (i.e., the primary signal dimension with respect to $\Delta S4(r)$) according to Equation (5). As yet another example, the signal representation of $P_r$ may be $\Delta S5(r)$ and the quantitative parameter may be ADC(r), wherein ADC(r) is associated with the b-value (i.e., the primary signal dimension with respect to $\Delta S5(r)$) according to Equation (6).

In some embodiments, the signal representation of the subject may be a processing result in K-space. The quantitative parameter may be any parameter that is associated with the processing result in K-space. In some embodiments, the quantitative parameter may be data in K-space. Alternatively, the quantitative parameter may be data in the image domain, wherein the determination of the value of the quantitative parameter may be performed in image reconstruction. For instance, by way of determining one or more quantitative parameters in the image domain from signal representation(s) in K-space, image reconstruction is achieved.

In some embodiments, the processing device 120 may obtain a relationship relating to signal representations of the subject and values of the quantitative parameter. The processing device 120 may further determine the value of the quantitative parameter of the subject based on a signal representation of the subject and the relationship. For example, the relationship may be described in the form of a correlation function, such as any of Equation (1) to Equation (6). The processing device 120 may determine the value of the quantitative parameter by solving the correlation function. As another example, the relationship may be presented in the form of a table or curve recording different signal representations and their corresponding values of the quantitative parameter. The processing device 120 may determine the value of the quantitative parameter by looking up the table or consulting the curve.

In some embodiments, the signal representation determined in operation 606 may be represented by a complex number including a phase component and an amplitude component. The value of the quantitative parameter may be determined based on at least one of the phase component or the amplitude component of the complex number. Alternatively, the signal representation may be represented by a real number, and the value of the quantitative parameter may be determined based on the real number. Taking the physical point $P_r$ as an example, the signal representation may be $\Delta S1(r)$ described above. If $\Delta S1(r)$ is a real number, $T^*_2(r)$ may be determined based on $\Delta S1(r)$. If $\Delta S1(r)$ is a complex number, $T^*_2(r)$ may be determined based on the amplitude component of $\Delta S1(r)$ according to Equation (7), and $\Delta B(r)$ may be determined based on the phase component of $\Delta S1(r)$ according to Equation (8) as below:

$$T^*_2(r) = -\Delta TE / \ln(|\Delta S1(r)|), \quad (7)$$

and $$\Delta B(r) = -\frac{\angle \Delta S1(r)}{\gamma \Delta TE}. \quad (8)$$

In some embodiments, the subject may be a physical point of a patient as described above. The patient may include one or more other physical points each of whose signal representation or value of a quantitative parameter is of interest. The processing device 120 may perform operation 608 for each physical point of the patient to determine a corresponding value of the quantitative parameter. The values of the quantitative parameter of the physical points may reflect one or more physiological or physical characteristics of different portions of the patient, and thereby can be used in disease diagnosis. Optionally, the processing device 120 may generate a quantitative parameter map (e.g., a T2 map, a T1 map) of the patient based on the values of the quantitative parameter of the physical points of the patient. The quantitative parameter map may be used for medical diagnosis.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may be accomplished with one or more additional operations not described and/or without one or more of the operations discussed above. For example, operation 608 may be omitted. In some embodiments, the order in which the operations of the process 600 described above is not intended to be limiting.

FIGS. 7A and 7B are flowcharts illustrating exemplary processes for determining a signal representation of a subject according to some embodiments of the present disclosure. In some embodiments, one or more operations of processes 700A and 700B may be implemented in the MRI system 100 illustrated in FIG. 1. For example, the process 700A and/or the process 700B may be stored in a storage device (e.g., the storage device 130, the storage 320, and/or the storage 490) of the MRI system 100 in the form of instructions, and invoked and/or executed by the processing device 120 (e.g., the processor 310 of the computing device 300 as illustrated in FIG. 3, the CPU 440 of the mobile device 400 as illustrated in FIG. 4, one or more modules as illustrated in FIG. 5).

In some embodiments, one or more operations of the process 700A may be performed to achieve at least part of operation 606 as described in connection with FIG. 6. In 702, for at least one value in the at least one secondary signal dimension, the processing device 120 (e.g., the determination module 504) may determine at least one preliminary signal representation of the subject associated with the primary signal dimension based on a portion of the plurality of signals that correspond to the value of the at least one secondary signal dimension.

For illustration purposes, the following description is provided with reference to the example in Table 1 as described in connection with FIG. 6. It is assumed that the signal representation to be determined is $\Delta S1(r)$ (i.e., the change of signal intensity at the physical point $P_r$ of the patient over $\Delta TE$). As described above, the primary signal dimension associated with $\Delta S1(r)$ may be the echo time, and the at least one secondary signal dimension may include the coil unit and the repetition. In some embodiments, for at least one coil unit (i.e., for at least one value in the dimension of coil unit) in each repetition (i.e., for at least one value in the dimension of repetition), the processing device 120 may determine at least one preliminary signal representation associated with the echo time.

Merely by way of example, for $Coil_1$ in $Repitition_1$, the processing device 120 may determine at least one preliminary signal representation based on the signals of $P_r$ corresponding to $Coil_1$ and $Repitition_1$, that is, $S_{e_1}^1(r)$ to $S_{e_n}^1(r)$ as illustrated in Table 1. The at least one preliminary signal representation may include $\Delta S_{2-1}^1(r)$, $S_{3-2}^1(r)$, ..., and $\Delta S_{n-(n-1)}^1(r)$, wherein $\Delta S_{i-(i-1)}^1(r)$ refers to a change of signal intensity with respect to $Coil_1$ in $Repitition_1$ at $P_r$ over a time interval between $TE_i$ and $TE_{i-1}$. $\Delta S_{i-(i-1)}^1(r)$ may be determined based on $S_{e_i}^1(r)$ and $S_{e_{i-1}}^1(r)$. For example, $\Delta S_{i-(i-1)}^1(r)$ may be equal to $S_{e_i}^1(r)/S_{e_{i-1}}^1(r)$. Similarly, the processing device 120 may determine at least one preliminary signal representation for each of the other coil units in $Repitition_1$ and each coil unit in $Repitition_2$. In this way, $2m*(n-1)$ preliminary signal representations of $P_r$ may be determined. In some embodiments, the processing device 120 may determine at least one preliminary signal representation for a portion of the coil units and/or a portion of the repetitions. In this way, fewer than $2m*(n-1)$ preliminary signal representations of $P_r$ may need to be determined.

It should be noted that the above description regarding the example in Table 1 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 120 may determine one preliminary signal representation (denoted as $\Delta S_1^1$) for $Coil_1$ in $Repitition_1$. $\Delta S_1^1$ may be equal to an average value of $\Delta S_{2-1}^1(r)$, $\Delta S_{3-2}^1(r)$, ..., and $\Delta S_{n-(n-1)}^1(r)$. Alternatively, the processing device 120 may determine $\Delta S_1^1$ by inputting $S_{e_1}^1(r)$ to $S_{e_n}^1(r)$ into an optimization function (e.g., Equation (9)) as described elsewhere in this disclosure (e.g., FIG. 7B and the relevant descriptions). In some embodiments, the at least one secondary signal dimension of the signals of the physical point $P_r$ described above is illustrative. The at least one secondary signal dimension of the signals of $P_r$ may include only one of the coil unit and repetition. Additionally or alternatively, the at least one secondary signal dimension of the signals of $P_r$ may further include one or more other secondary signal dimensions, such as one or more imaging parameters of the MRI device.

In 704, the processing device 120 (e.g., the determination module 504) may determine the signal representation of the subject based on at least a portion of the at least one preliminary signal representation of the subject.

In some embodiments, the signal representation may be a sum, an average value, or a median value of the at least a portion of the at least one preliminary signal representation. In some embodiments, all of the at least one preliminary signal representation determined in operation 702 may be used to determine the signal representation of the subject. Alternatively, only a portion of the at least one preliminary signal representation determined in operation 702 may be used to determine the signal representation of the subject. Taking the example illustrated in Tablet as an instance, the processing device 120 may determine the signal representation based on the preliminary signal representations corresponding to $Coil_1$ to $Coil_{m-1}$, for example, if $Coil_m$ has some operation faults.

In some embodiments, one or more operations of the process 700B may be performed to achieve at least part of operation 606 as described in connection with FIG. 6. In 706, the processing device 120 (e.g., the acquisition module 502) may obtain an optimization function of the signal representation of the subject, wherein the optimization function may incorporate the primary signal dimension and the at least one secondary signal dimension.

Taking the example illustrated in Table 1 as an example, the optimization function may be an Equation (9) as below:

$$\mathrm{argmin}_{\Delta S1(r)} \Sigma_i^{N_{ech}-1} \Sigma N_{ch} N_{acq} \|S_{e_{i+1}}(r) - S_{e_i}(r) \Delta S1(r)\|_2^2, \quad (9)$$

where $N_{ech}$ refers the count of values in the echo time dimension (i.e., n), $N_{ch}$ refers to the count of values in the coil unit (i.e., m), $N_{acq}$ refers to the count of values in the repetition (i.e., 2 in the example in Table 1), and $S_{e_{i+1}}(r)$ and $S_{e_i}(r)$ refer to a pair of signals corresponding to two successive echo signals detected by one coil unit in one repetition. It should be noted that the Equation (9) illustrated above is merely provided for the purposes of illustration, and not intended to limit the scope of the present disclosure. In some embodiments, the signals of the physical point $P_r$ may have one or more other secondary signal dimensions, and the other secondary signal dimension(s) may be incorporated in the Equation (9), for example, in a similar manner as the coil unit and the repetition.

In 708, the processing device 120 (e.g., the determination module 504) may determine the signal representation of the subject by inputting the signals of the subject into the optimization function.

Taking the physical point $P_r$ as an example, the processing device 120 may input the signals (i.e., $S_{e_1}^1(r)$ to $S_{e_n}^m(r)$) into Equation (9) and solve Equation (9) to determine $\Delta S1(r)$. In some embodiments, the processing device 120 may solve the optimization function using a least square method, a neural network model, a support vector machine (SVM), or the like, or any combination thereof.

In some embodiments, for at least one value in the at least one secondary signal dimension, the processing device 120 may determine, among the plurality of signals of the subject, at least one pair of signals corresponding to the value in the at least one secondary signal dimension. Each pair of the at least one pair of signals may correspond to different values in the primary signal dimension. For example, for Coil$_1$ in Repitition$_1$, the processing device 120 may determine (n−1) pairs of signals corresponding to successive echo signals detected by Coil$_1$ in Repitition$_1$, such as a first pair of $S_{e_1}^{\ 1}(r)$ and $S_{e_2}^{\ 1}(r)$, a second pair of $S_{e_2}^{\ 1}(r)$ and $S_{e_3}^{\ 1}(r)$, or the like. The processing device 120 may further determine the signal representation of the subject by inputting the at least one pair of signals into the optimization function. For example, the at least one pair of signals may be inputted into Equation (9) to determine $\Delta S1(r)$.

In the processes 700A and 700B, the signal representation of the subject is determined by jointly processing signals of different signal dimensions, including the primary signal dimension and the at least one secondary signal dimension. This may improve the efficiency and/or accuracy of signal representation determination compared with processing signals of different signal dimensions independently. For example, in the process 700A, one or more preliminary signal representations may be determined for each coil unit (i.e., for each value in a secondary signal dimension). The signal representation of the subject may be determined based on the preliminary signal representations of all coil units of the MRI device. For example, the signal representation of the subject may be an average of the preliminary signal representations of all coil units of the MRI device. In addition, in some embodiments, a preliminary signal representation may be determined based on a comparison between signals detected by different coil units, for example, the preliminary signal representation for $P_r$ may be equal $S_{e_i}^{\ 1}(r)/S_{e_{i-1}}^{\ 1}(r)$ as described above. This may reduce the influence of coil performance (e.g., a sensitivity distribution, a signal-to-noise ratio (SNR)) on the signal representation, thereby improving the accuracy of the determined signal representation. As another example, in the process 700B, an optimization function, which incorporates and processes both the primary signal dimension and the at least one secondary signal dimension, is utilized to determine the signal representation of the subject, which may improve computational efficiency and reduce processing time.

It should be noted that the above descriptions regarding the processes 700A and 700B are merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

EXAMPLES

The examples are provided for illustration purposes, and not intended to limit the scope of the present disclosure.

FIGS. 8A to 8E are schematic diagrams illustrating exemplary T2*-quantitative maps 800A to 800E of a knee of a patient according to some embodiments of the present disclosure.

As shown in FIGS. 8A to 8E, each T2*-quantitative map may include a plurality of pixels representing a plurality of physical points of the knee. The pixel value of each pixel in each T2*-quantitative map may be determined based on a calculated value of T2* of the corresponding physical point. An MRI device was caused to apply a multi-echo pulse sequence on the knee of the patient, and a plurality of echoes sequentially occurred at different TEs. Each coil unit of the MRI device detected a plurality of echo signals corresponding to the echoes. For each coil unit, a plurality of images of the knee corresponding to the plurality of echoes were obtained by image reconstruction based on the corresponding echo signals. The pixel values of the pixels in the T2*-quantitative maps 800A to 800E were determined based on the images of the coil units in different ways. For illustration purposes, the determination of pixel values corresponding to a physical point $P_k$ in the T2*-quantitative maps 800A to 800E is described as an example.

In the T2*-quantitative map 800A, the pixel value corresponding to $P_k$ was determined based on a first value of T2* of $P_k$, wherein the first value was determined by performing a method (e.g., the process 600) disclosed in the present disclosure.

In the T2*-quantitative map 800B, the pixel value corresponding to $P_k$ was determined based on a second value of T2* of $P_k$. In some embodiments, after the images were reconstructed, the processing device 120 generated an echo image for each echo by combining the corresponding images of different coil units according to an adaptive coil combination (ACC) algorithm. The processing device 120 further determined the second value of T2* of $P_k$ based on the echo images according to a method (e.g., the process 600) disclosed in the present disclosure. For example, the processing device 120 designated image data corresponding to $P_k$ in the echo images as a plurality of signals of $P_k$. The processing device 120 further performed operations 604 to 608 to determine the second value of T2* of $P_k$.

The pixel values of $P_k$ in the T2*-quantitative maps 800C, 800D, and 800E were determined based on a third value, a fourth value, and a fifth value of T2* of $P_k$, respectively. In some embodiments, the image data corresponding to $P_k$ in the echo images described above may reflect signal intensities at $P_k$ at different TEs. The processing device 120 determined the third, the fourth, and the fifth value of T2* of $P_k$ by fitting the image data in the echo images with different fitting models of signal intensity. As an example, the third, the fourth, and the fifth value were determined based on a 3-parameter model (1), a 2-parameter exponential model (2), and a 2-parameter linear model (3), respectively, as below:

$$S(TE)=S_0 e^{-TE/T^*_2(1)}+S_{offset}, \qquad \text{Model (1)}$$

$$S(TE)=S_0 e^{-TE/T^*_2(2)}, \qquad \text{Model (2)}$$

and $$\ln(S(TE))=\ln(S_0)-TE/T^*_2(3). \qquad \text{Model (3)}$$

where $S_0$ refers to a theoretical signal intensity when TE=0, $S_{offset}$ refers to a signal intensity of a baseline signal, $T^*_2(1)$ refers to the third value, $T^*_2(2)$ refers to the fourth value, and $T^*_2(3)$ refers to the fifth value.

As shown in FIGS. 8A to 8E, the T2*-quantitative maps 800A to 800E have different SNRs. For example, compared with the T2*-quantitative maps 800B to 800E, the T2*-quantitative map 800A has fewer white dots and is more smooth, showing a higher SNR. This suggests that the method disclosed in the present disclosure can be used to generate a T2*-quantitative map with a higher image quality and a lower SNR.

Figure 9A:
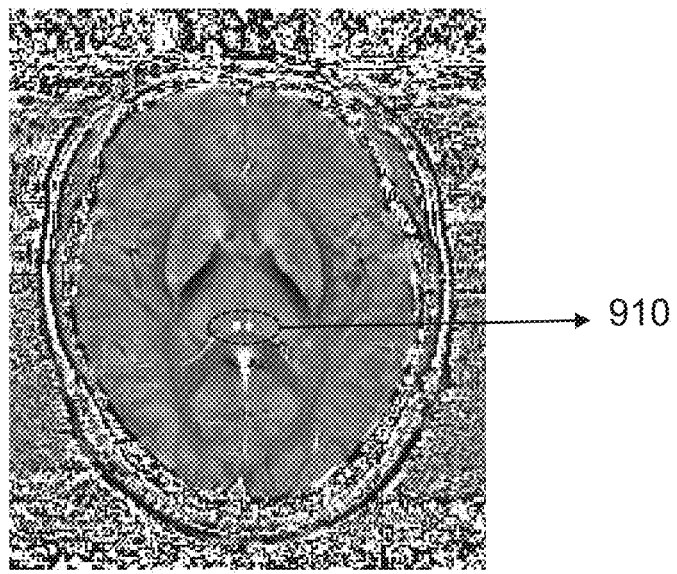
FIGS. 9A and 9B are schematic diagrams illustrating exemplary local field maps of a brain of a patient according to some embodiments of the present disclosure.
Figure 9B:
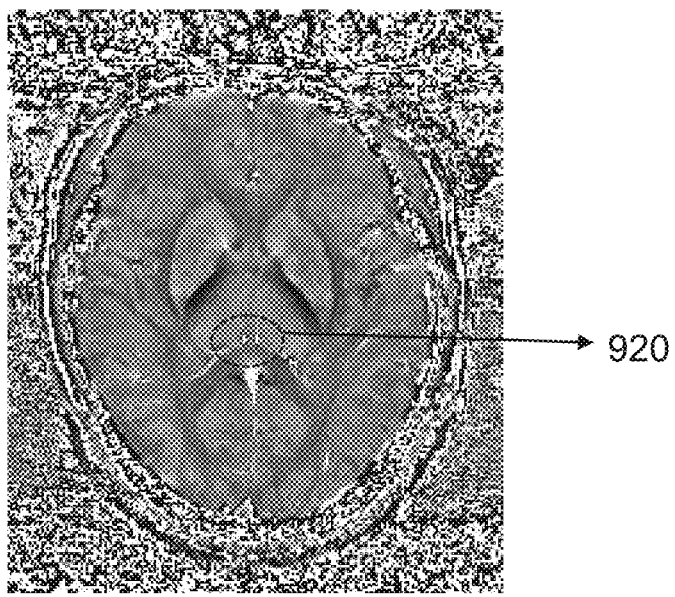

FIGS. 9A and 9B are schematic diagrams illustrating exemplary local field maps 900A and 900B of a brain of a patient according to some embodiments of the present disclosure.

As shown in FIGS. 9A and 9B, each of the local field maps 900A and 900B may include a plurality of pixels representing a plurality of physical points of the brain. The pixel value of each pixel in the local field maps 900A and 900B were determined based on a calculated value of a local field intensity of the corresponding physical point. In some embodiments, an MRI device was caused to apply a multi-echo pulse sequence on the knee of the patient, and a plurality of echoes sequentially occurred at different TEs. Each coil unit of the MRI device detected a plurality of echo signals corresponding to the echoes. For each coil unit, a plurality of images of the brain corresponding to the plurality of echoes were obtained by image reconstruction based on the corresponding echo signals. The pixel values of the pixels in the local field maps 900A and 900B were determined based on the reconstructed images of the brain in different ways. For illustration purposes, the determination of pixel values corresponding to a physical point $P_q$ in the local field maps 900A and 900B is described as an example.

In the local field map 900A, the pixel value corresponding to $P_q$ was determined based on a first value of a local field distribution at $P_q$, wherein the first value was determined by performing a method (e.g., the process 600) disclosed in the present disclosure.

In the local field map 900B, the pixel value corresponding to $P_q$ was determined based on a second value of the local field distribution at $P_q$. In some embodiments, the processing device 120 first performed a phase correction (e.g., a phase offset removal) on the phase components of the images. The processing device 120 further generated an echo image for each echo by combining the phase components in the corresponding corrected images of different coil units. The processing device 120 then determined the second value of the local field distribution at $P_q$ by fitting image data corresponding to $P_q$ in the echo images with a linear model.

As shown in FIGS. 9A and 9B, the local field maps 900A and 900B have different SNRs. For example, compared with the local field map 900B, two bright spots 910 in FIG. 9A are more clear and apparent than two bright spots 920 in FIG. 9B, suggesting that the local field distribution of small tissues in the local field map 900A is more accurate than that in the local field map 900B.

It should be noted that the above examples illustrated in FIGS. 8A to 9B are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially," For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A magnetic resonance imaging (MRI) system, comprising:
at least one storage medium including a set of instructions for determining a signal representation of a subject in MRI; and
at least one processor configured to communicate with the at least one storage medium, wherein when executing the set of instructions, the at least one processor is configured to direct the system to perform operations including:
acquiring a plurality of signals of the subject, the plurality of signals being generated using an MRI device, each of the plurality of signals corresponding to a set of values in a plurality of signal dimensions, each of the plurality of signal dimensions of the signal describing an instance under which the signal is determined or acquired using the MRI device;
determining, among the plurality of signal dimensions, a primary signal dimension and at least one secondary signal dimension, the primary signal dimension being associated with the signal representation;
determining, based on the plurality of signals, the primary signal dimension, and the at least one secondary signal dimension, the signal representation of the subject; and
determining, based on the signal representation of the subject, a value of a quantitative parameter of interest of the subject, the signal representation and the primary signal dimension being associated with the quantitative parameter of interest, the at least one secondary signal dimension being not associated with the quantitative parameter of interest, wherein the signal representation is represented by a complex number including a phase component and an amplitude component, and the value of the quantitative parameter of interest is determined based on at least one of the phase component or the amplitude component of the complex number, or the signal representation is represented by a real number, and the value of the quantitative parameter of interest is determined based on the real number.

2. The system of claim 1, wherein to determine the signal representation of the subject, the at least one processor is further configured to direct the system to perform additional operations including:
for at least one value in the at least one secondary signal dimension, determining, based on a portion of the plurality of signals that correspond to the value of the at least one secondary signal dimension, at least one preliminary signal representation of the subject associated with the primary signal dimension; and
determining, based on at least a portion of the at least one preliminary signal representation of the subject, the signal representation of the subject.

3. The system of claim 1, wherein to determine the signal representation of the subject, the at least one processor is further configured to direct the system to perform additional operations including:
obtaining an optimization function of the signal representation of the subject, the optimization function incorporating the primary signal dimension and the at least one secondary signal dimension; and
determining the signal representation of the subject by inputting the plurality of signals into the optimization function.

4. The system of claim 3, wherein to determine the signal representation of the subject by inputting the plurality of signals into the optimization function, the at least one processor is further configured to direct the system to perform additional operations including:
  for at least one value in the at least one secondary signal dimension, determining, among the plurality of signals, at least one pair of signals corresponding to the value in the at least one secondary signal dimension, wherein each pair of the at least one pair of signals corresponds to different values in the primary signal dimension; and
  determining the signal representation of the subject by inputting the at least one pair of signals into the optimization function.

5. The system of claim 1, wherein to acquire a plurality of signals of the subject, the at least one processor is further configured to direct the system to perform additional operations including:
  causing the MRI device to apply an MR pulse sequence on the subject;
  detecting, by at least one coil units of the MRI device, a plurality of echo signals; and
  determining, based on the plurality of echo signals, the plurality of signals of the subject.

6. The system of claim 5, wherein the subject is a physical point of an object, and to determine the plurality of signals of the subject based on the plurality of echo signals, the at least one processor is further configured to direct the system to perform additional operations including:
  reconstructing, based on the plurality of echo signals, a plurality of images including image data of the physical point; and
  designating the image data corresponding to the physical point in the plurality of images as the plurality of signals of the physical point.

7. The system of claim 1, wherein to determine a value of the quantitative parameter of interest of the subject, the at least one processor is further configured to direct the system to perform additional operations including:
  obtaining a relationship relating to signal representations of the subject and values of the quantitative parameter of interest; and
  determining, based on the signal representation of the subject and the relationship, the value of the quantitative parameter of interest of the subject.

8. The system of claim 1, wherein the subject is a physical point of an object, the signal representation is a change of signal intensity at the physical point with an echo time, and
  the quantitative parameter of interest of the physical point includes at least one of a longitudinal relaxation time, a transverse relaxation time, an apparent diffusion coefficient (ADC), a transverse relaxation decay, a field distribution, or a longitudinal relaxation time in a rotating frame.

9. The system of claim 8, wherein:
  the primary signal dimension is an echo time, and the quantitative parameter of interest is at least one of the transverse relaxation time, the transverse relaxation decay, or the field distribution, or
  the primary signal dimension is a T2-preparation duration, and the quantitative parameter of interest is the transverse relaxation time, or
  the primary signal dimension is a T1$\rho$-preparation duration, and the quantitative parameter of interest is the longitudinal relaxation time in a rotating frame, or
  the primary signal dimension is an inversion time, and the quantitative parameter of interest is the longitudinal relaxation time, or
  the primary signal dimension is a b-value, and the quantitative parameter of interest is the ADC.

10. The system of claim 1, wherein the plurality of signal dimensions include at least two of an echo time (TE), a unit repetition time (TR), an inversion recovery time (TI), a b-value, a T1$\rho$-preparation duration, a T2-preparation duration, a repetition, a velocity encoding value, a count of radio frequency (RF) channels, a flip angle, an RF center frequency, or an RF receiving coil unit.

11. A method, that is implemented on a computing device having at least one processor and at least one storage medium including a set of instructions for determining a signal representation of a subject in magnetic resonance imaging (MRI), the method comprising:
  acquiring a plurality of signals of the subject, the plurality of signals being generated using an MRI device, each of the plurality of signals corresponding to a set of values in a plurality of signal dimensions, each of the plurality of signal dimensions of the signal describing an instance under which the signal is determined or acquired using the MRI device;
  determining, among the plurality of signal dimensions, a primary signal dimension and at least one secondary signal dimension, the primary signal dimension being associated with the signal representation;
  determining, based on the plurality of signals, the primary signal dimension, and the at least one secondary signal dimension, the signal representation of the subject; and
  determining, based on the signal representation of the subject, a value of a quantitative parameter of interest of the subject, the signal representation and the primary signal dimension being associated with the quantitative parameter of interest, the at least one secondary signal dimension being not associated with the quantitative parameter of interest, wherein
    the signal representation is represented by a complex number including a phase component and an amplitude component, and the value of the quantitative parameter of interest is determined based on at least one of the phase component or the amplitude component of the complex number, or
    the signal representation is represented by a real number, and the value of the quantitative parameter of interest is determined based on the real number.

12. The method of claim 11, wherein the determining the signal representation of the subject further comprises:
  for at least one value in the at least one secondary signal dimension, determining, based on a portion of the plurality of signals that correspond to the value of the at least one secondary signal dimension, at least one preliminary signal representation of the subject associated with the primary signal dimension; and
  determining, based on at least a portion of the at least one preliminary signal representation of the subject, the signal representation of the subject.

13. The method of claim 11, wherein the determining the signal representation of the subject further comprises:
  obtaining an optimization function of the signal representation of the subject, the optimization function incorporating the primary signal dimension and the at least one secondary signal dimension; and
  determining the signal representation of the subject by inputting the plurality of signals into the optimization function.

14. The method of claim 13, wherein the determining the signal representation of the subject by inputting the plurality of signals into the optimization function further comprises:
  for at least one value in the at least one secondary signal dimension, determining, among the plurality of signals, at least one pair of signals corresponding to the value in the at least one secondary signal dimension, wherein each pair of the at least one pair of signals corresponds to different values in the primary signal dimension; and determining the signal representation of the subject by inputting the at least one pair of signals into the optimization function.

15. The method of claim 11, wherein the subject is a physical point of an object, the signal representation is a change of signal intensity at the physical point with an echo time, and the quantitative parameter of interest of the physical point includes at least one of a longitudinal relaxation time, a transverse relaxation time, an apparent diffusion coefficient (ADC), a transverse relaxation decay, a field distribution, or a longitudinal relaxation time in a rotating frame.

16. The method of claim 15, wherein:

the primary signal dimension is an echo time, and the quantitative parameter of interest is at least one of the transverse relaxation time, the transverse relaxation decay, or the field distribution, or the primary signal dimension is a T2-preparation duration, and the quantitative parameter of interest is the transverse relaxation time, or the primary signal dimension is a T1ρ-preparation duration, and the quantitative parameter of interest is the longitudinal relaxation time in a rotating frame, or the primary signal dimension is an inversion time, and the quantitative parameter of interest is the longitudinal relaxation time, or the primary signal dimension is a b-value, and the quantitative parameter of interest is the ADC.

17. A non-transitory readable medium, comprising at least one set of instructions for determining a signal representation of a subject in magnetic resonance imaging (MRI), wherein when executed by at least one processor of an electrical device, the at least one set of instructions directs the at least one processor to perform a method, the method comprising:

acquiring a plurality of signals of the subject, the plurality of signals being generated using an MRI device, each of the plurality of signals corresponding to a set of values in a plurality of signal dimensions, each of the plurality of signal dimensions of the signal describing an instance under which the signal is determined or acquired using the MRI device;

determining, among the plurality of signal dimensions, a primary signal dimension and at least one secondary signal dimension, the primary signal dimension being associated with the signal representation;

determining, based on the plurality of signals, the primary signal dimension, and the at least one secondary signal dimension, the signal representation of the subject; and determining, based on the signal representation of the subject, a value of a quantitative parameter of interest of the subject, the signal representation and the primary signal dimension being associated with the quantitative parameter of interest, the at least one secondary signal dimension being not associated with the quantitative parameter of interest, wherein the signal representation is represented by a complex number including a phase component and an amplitude component, and the value of the quantitative parameter of interest is determined based on at least one of the phase component or the amplitude component of the complex number, or the signal representation is represented by a real number, and the value of the quantitative parameter of interest is determined based on the real number.

18. The non-transitory readable medium of claim 17, wherein the determining the signal representation of the subject comprises:

for at least one value in the at least one secondary signal dimension, determining, based on a portion of the plurality of signals that correspond to the value of the at least one secondary signal dimension, at least one preliminary signal representation of the subject associated with the primary signal dimension; and determining, based on at least a portion of the at least one preliminary signal representation of the subject, the signal representation of the subject.

19. The non-transitory readable medium of claim 17, wherein the determining the signal representation of the subject comprises:

obtaining an optimization function of the signal representation of the subject, the optimization function incorporating the primary signal dimension and the at least one secondary signal dimension; and determining the signal representation of the subject by inputting the plurality of signals into the optimization function.

20. The non-transitory readable medium of claim 19, wherein the determining the signal representation of the subject by inputting the plurality of signals into the optimization function comprises:

for at least one value in the at least one secondary signal dimension, determining, among the plurality of signals, at least one pair of signals corresponding to the value in the at least one secondary signal dimension, wherein each pair of the at least one pair of signals corresponds to different values in the primary signal dimension; and determining the signal representation of the subject by inputting the at least one pair of signals into the optimization function.

* * * * *